United States Patent [19]
Fujita et al.

[11] Patent Number: 5,385,877
[45] Date of Patent: Jan. 31, 1995

[54] PRODUCTION OF ALPHA-OLEFIN POLYMERS

[75] Inventors: Takashi Fujita; Toshihiko Sugano; Hideshi Uchino, all of Yokkaichi, Japan

[73] Assignee: Mitsubishi Petrochemical Company Limited, Tokyo, Japan

[21] Appl. No.: 832,322

[22] Filed: Feb. 7, 1992

[30] Foreign Application Priority Data

Feb. 7, 1991 [JP] Japan .................... 3-016583

[51] Int. Cl.$^6$ .................... C08F 4/602; C08F 10/00
[52] U.S. Cl. .................... 502/103; 502/117; 526/153; 526/127; 526/160; 526/348.5; 526/351; 526/352
[58] Field of Search .................... 526/153, 160; 502/103

[56] References Cited

U.S. PATENT DOCUMENTS

| | | | |
|---|---|---|---|
| 4,978,730 | 12/1990 | Maezawa et al. | 526/165 |
| 5,003,019 | 3/1991 | Ishimaru | 526/160 |
| 5,006,500 | 4/1991 | Chang | 526/129 |
| 5,086,024 | 2/1992 | Crapo et al. | 526/165 |

FOREIGN PATENT DOCUMENTS

| | | |
|---|---|---|
| 285443 | 10/1988 | European Pat. Off. |
| 0372617 | 6/1990 | European Pat. Off. |
| WO91/05810 | 5/1991 | WIPO |

OTHER PUBLICATIONS

Boor, Ziegler–Natta Catalysts and Polymerizations, Academic Press, Jun. (N.Y.) 1979 602–609.
Chemical Abstracts, vol. 115, No. 16, Oct. 21, 1991, 160019J, "Manufucture of Olefin Polymers in Presence of Aluminoxane-Containing Catalysts".
Chemical Abstracts, vol. 115, No. 15, Oct. 14, 1991, 159433H, "Process for the Preparation of Solutions of Oligomeric Methylalumoxanes".

*Primary Examiner*—Edward J. Smith
*Attorney, Agent, or Firm*—Oblon, Spivak, McClelland, Maier & Neudstadt

[57] ABSTRACT

A catalyst for α-olefin polymerization which comprises the following components (A) and (B):
component (A), which is a transition metal compound represented by the formula $$Q(C_5H_{4-m}R^1{}_m)(C_5H_{4-n}R^2{}_n)MeXY$$

wherein $(C_5H_{4-m}R^1{}_m)$ and $(C_5H_{4-n}R^2{}_n)$ respectively represent a conjugated five-membered ring ligand coordinating to a metal Me; $R^1$ and $R^2$ which may be the same or different and a plurality of each of which can be bonded together, respectively represent a hydrocarbyl group having 1 to 20 carbon atoms, a halogen atom, an alkoxy group, a silicon-containing hydrocarbyl group, a phosphorus-containing hydrocarbyl group, a nitrogen-containing hydrocarbyl group or a boron-containing hydrocarbyl group; Q represents a bonding group which crosslinks the two conjugated five-membered ring ligand; Me represents a transition metal of the IVB-VIB group in the Periodic Table; X and Y, which may be the same or different, respectively represent hydrogen, a halogen atoms, a hydrocarbyl group, an alkoxy group, an amino group, a phosphorus-containing hydrocarbyl group or a silicon-containing hydrocarbyl group; m denotes an integer of $0 \leq m \leq 4$ and n denotes an integer of $0 \leq n \leq 4$; component (B), which is a methylisobutylalumoxane which satisfies the following conditions (a), (b) and (c): (a) the molar ratio of a methyl group to an isobutyl group being in the range of 4:1 to 1:4, (b) the chemical shift of $^{27}$Al-NMR being in the range of 160 ppm to 250 ppm and the peak having a half-height width of no smaller than 3000 Hz, and (c) it has a repeating unit of Al—O in an amount of 2 to 100. The methylisobutylalumoxane is assumed to be novel.

12 Claims, 4 Drawing Sheets

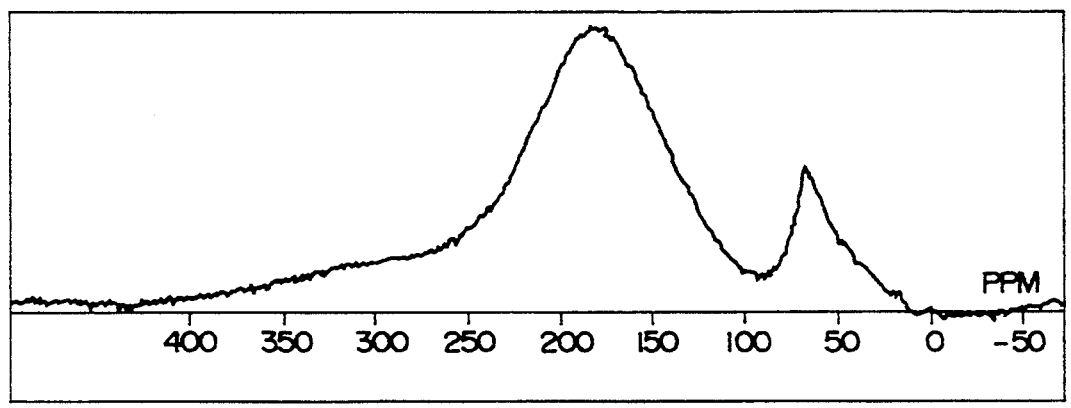
F I G . 2
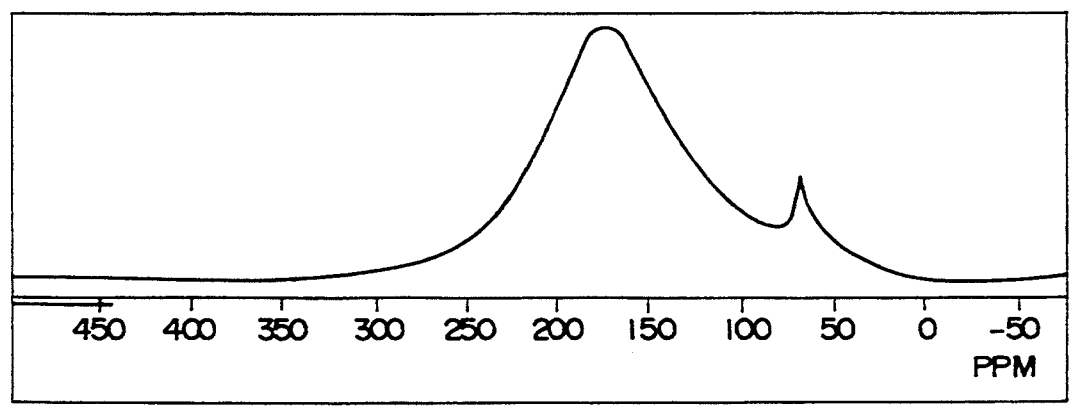
F I G . 3

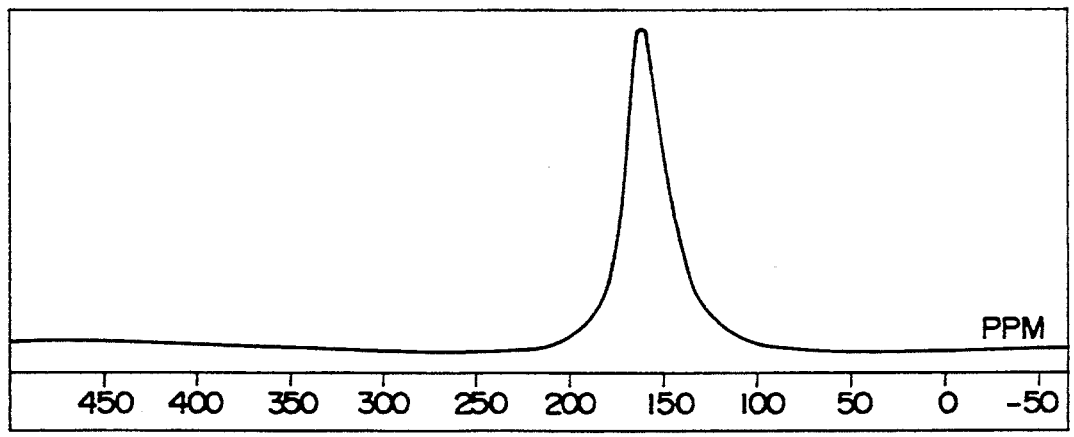
F I G. 4
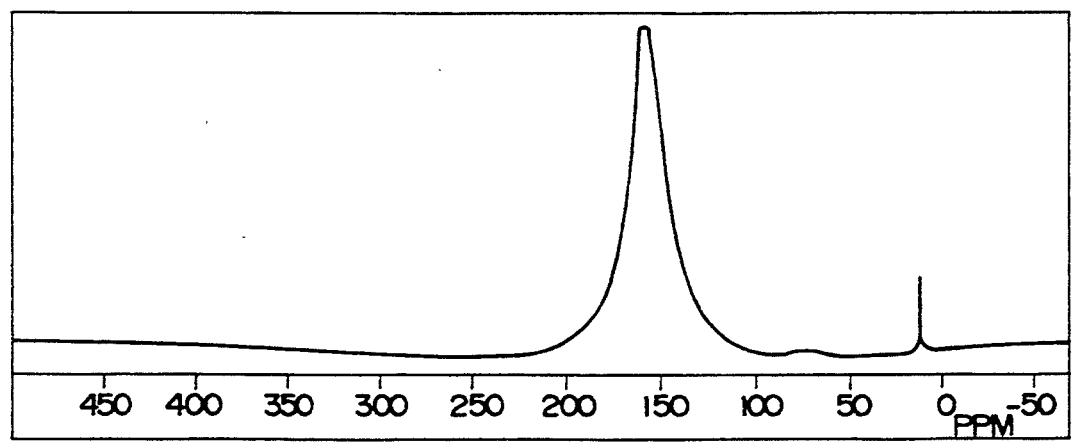
F I G. 5

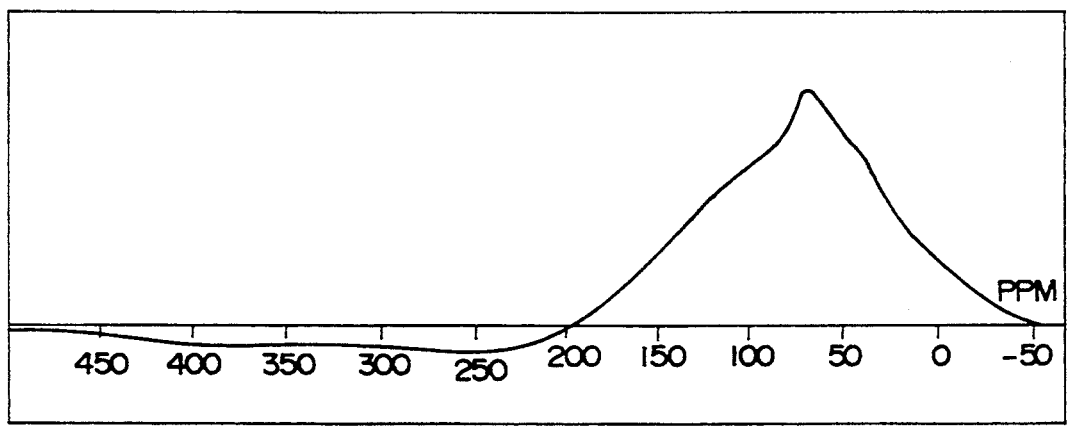
F I G . 6
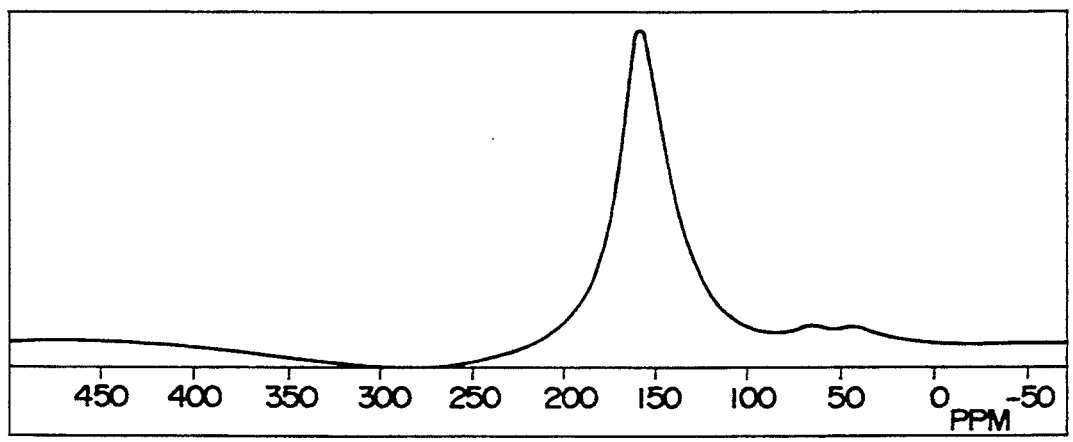
F I G . 7
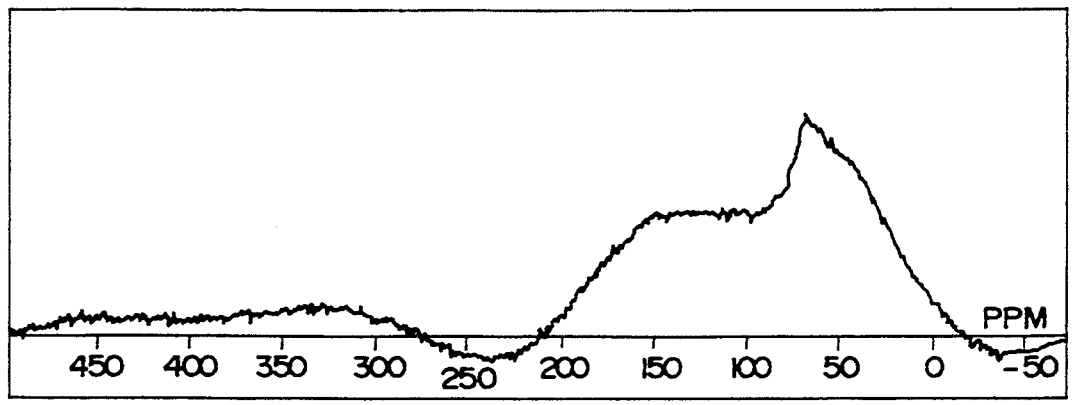
F I G . 8

PRODUCTION OF ALPHA-OLEFIN POLYMERS

BACKGROUND OF THE INVENTION

The present invention relates to a process for preparing α-olefin polymers. More particularly, the present invention relates to a catalyst for polymerization of α-olefins comprising a specific transition metal compound and a specific novel methylisobutylalumoxane and a process for preparing poly-α-olefins.

RELATED ART

The methods of preparing poly-α-olefins wherein a catalyst comprising an alumoxane and a transition metal compound in combination are well-known (Japanese Patent Laid-Open Publication Nos. 45205/1983, 19309/1983, 35007/1985, 130314/1986, 230802/1987, 142004/1988, 234009/1988, 51408/1989 and 66214/1989). These techniques may, however, have high production cost due to the low activities per aluminum and industrial disadvantages due to the large amounts of aluminum remaining in olefin polymers.

For the purpose of solving the problems, a variety of proposals have been disclosed in Japanese Patent Laid-Open Publication Nos. 211307/1986, 130601/1988, 16803/1989, 22308/1990 and 167307/1990. The activity per aluminum have been improved to some extent in these proposals. However, alumoxane has poor solubility and is hard to deal with in its nature, and the difficulty of removing aluminum may bring about the lowering of quality or the deterioration of hue of olefin polymers thereby produced, so that further improvement is required.

As alternative proposals, the methods where use is made of another organoaluminum compound or the like in addition to methylalumoxane have also been described in Japanese Patent Laid-Open Publication Nos. 260602/1985, 130604/1985, 89506/1988, 178108/1988, 218707/1988, 9206/1989, 315407/1989, 22306/1990 and 167310/19901. Although these methods have successively decreased the amount of methylalumoxane used, the activity per aluminum may still be unsatisfactory and thus further improvement may be desired.

On the other hand, a catalyst component for olefin polymerization comprising an alumoxane compound containing at least two alkyl groups has been described as a new proposal in Japanese Patent Laid-Open Publication Nos. 247201/1990, and 250886/1990 and U.S. Pat. No. 5,003,095. To the best of our knowledge, however, the method may improve the activity only insufficiently, and thus further improvement of the activity may be desired.

SUMMARY OF THE INVENTION

The object of the present invention is to solve aforementioned many problems in the prior art.

The present invention in one aspect, provides catalyst for α-olefin polymerization which comprises the following components (A) and (B):

component (A), which is a transition metal compound represented by the formula $$Q(C_5H_{4-m}R^1_m)(C_5H_{4-n}R^2_n)MeXY$$

wherein $(C_5H_{4-m}R^1_m)$ and $(C_5H_{4-n}R^2_n)$ respectively represent a conjugated five-membered ring ligand coordinating to a metal Me; $R^1$ and $R^2$ which may be the same or different and a plurality of each of which can be bonded together, respectively represent a hydrocarbyl group having 1 to 20 carbon atoms, a halogen atom, an alkoxy group, a silicon-containing hydrocarbyl group, a phosphorus-containing hydrocarbyl group, a nitrogen-containing hydrocarbyl group or a boron-containing hydrocarbyl group; Q represents a bonding group which crosslinks the two conjugated five-membered ring ligands; Me represents a transition metal of the IVB-VIB group in the Periodic Table; X and Y, which may be the same or different, respectively represent hydrogen, a halogen atoms, a hydrocarbyl group, an alkoxy group, an amino group, a phosphorus-containing hydrocarbyl group or a silicon-containing hydrocarbyl group; m denotes an integer of $0 \leq m \leq 4$ and n denotes an integer of $0 \leq n \leq 4$;

component (B), which is a methylisobutylalumoxane which satisfies the following conditions (a), (b) and (c):

(a) the molar ratio of a methyl group to an isobutyl group is in the range of 4:1 to 1:4, (b) the chemical shift of $^{27}$Al-NMR is in the range of 160 ppm to 250 ppm and the peak has a half-height width of no smaller than 3000 Hz, and (c) it has a repeating unit of Al—O in an amount of 2 to 100.

The present invention, in another aspect, provides a process for preparing α-olefin polymers which comprises contacting an α-olefin with a catalyst for α-olefin polymerization thereby to polymerize the α-olefins, the catalyst comprising the following components (A) and (B):

component (A), which is a transition metal compound represented by the formula $$Q(C_5H_{4-m}R^1_m)(C_5H_{4-n}R^2_n)MeXY$$

wherein $(C_5H_{4-m}R^1_m)$ and $(C_5H_{4-n}R^2_n)$ respectively represent a conjugated five-membered ring ligand coordinating to a metal Me; $R^1$ and $R^2$, which may be the same or different and a plurality of each of which can be bonded together, respectively represent a hydrocarbyl group having 1 to 20 carbon atoms, a halogen atom, an alkoxy group, a silicon-containing hydrocarbyl group, a phosphorus-containing hydrocarbyl group, a nitrogen-containing hydrocarbyl group or a boron-containing hydrocarbyl group; Q represents a bonding group which crosslinks the two conjugated five-membered ring ligands; Me represents a transition metal of the IVB-VIB group in the Periodic Table; X and Y, which may be the same or different, respectively represent hydrogen, a halogen atoms, a hydrocarbyl group, an alkoxy group, an amino group, a phosphorus-containing hydrocarbyl group or a silicon-containing hydrocarbyl group; m denotes an integer of $0 \leq m \leq 4$ and n denotes an integer of $0 \leq n \leq 4$;

component (B), which is a methylisobutylalumoxane which satisfies the following conditions (a), (b) and (c):

(a) the molar ratio of a methyl group to an isobutyl group is in the range of 4:1 to 1:4, (b) the chemical shift of $^{27}$Al-NMR is in the range of 160 ppm to 250 ppm and the peak has a half-height width of no smaller than 3000 Hz, and (c) it has a repeating unit of Al—O in an amount of 2 to 100.

BRIEF DESCRIPTION OF THE DRAWINGS

FIG. 2 is a $^{27}$Al-NMR spectrum of the component (B) prepared in Example 1,

FIG. 3 is a $^{27}$Al-NMR spectrum of the component (B) prepared in Example 2,

FIG. 4 is a $^{27}$Al-NMR spectrum of a commercially available polymethylalumoxane, FIG. 5 is a $^{27}$Al-NMR spectrum of a commercially available polymethylalumoxane, FIG. 6 is a $^{27}$Al-NMR spectrum of a commercially available polyisobutylalumoxane, FIG. 7 is a $^{27}$Al-NMR spectrum of the alumoxane in Comparative Example 4, and FIG. 8 is a $^{27}$Al-NMR spectrum of the alumoxane in Comparative Example 5.

DETAILED DESCRIPTION OF THE INVENTION

<Catalyst of α-olefin polymerization>

Figure 1:
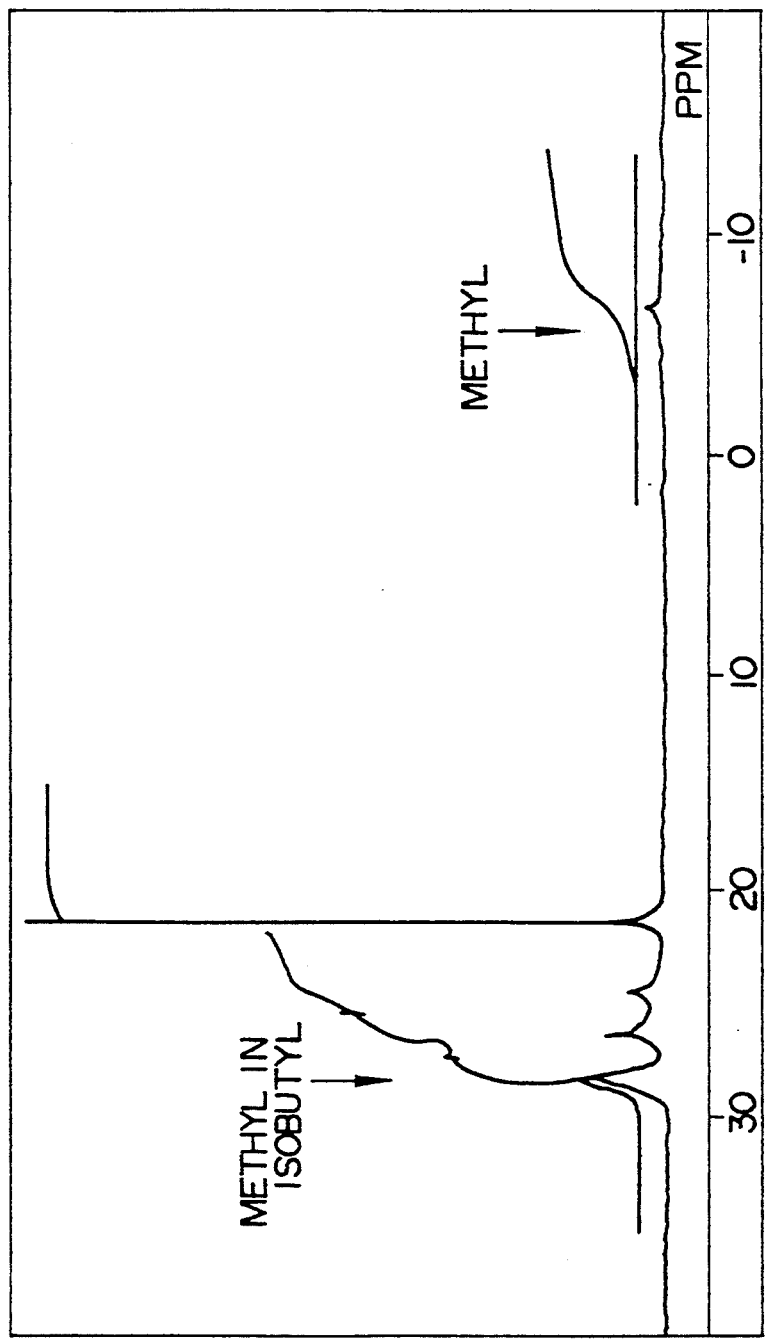
FIG. 1 is a $^{13}$C-NMR spectrum of the component (B) prepared in Example 1.

The catalyst of α-olefin polymerization of the present invention comprises the components (A) and (B). The term "comprises" herein used does not intend to exclude any optional or third component as far as they will not adversely affect the effects of the components (A) and (B).

Component (A)

The component (A) is a transition metal compound represented by the formula:

$$Q(C_5H_{4-m}R^1_m)(C_5H_{4-n}R^2_n)MeXY$$

The compound has a structure in which two conjugated five-membered ring groups $C_5H_{4-m}R^1_m$ and $C_5H_{4-n}R^2_n$ crosslinked with the crosslinking group Q, that is, $Q(C_5H_{4-m}R^1_m)(C_5H_{4-n}R^2_n)$, coordinate the transition metal compound MeXY of the IVB-VIB group in the Periodic Table.

In this connection, while the conjugated five-membered ring groups $C_5H_{4-m}R^1_m$ and $C_5H_{4-n}R^2_n$ have been separately defined, m and n and $R^1$ and $R^2$ have the same meaning, respectively (as will be described in detail), so that it is needless to say that these two conjugated five-membered ring groups may be the same or different. A specific example of the conjugated five-membered ring groups is the one wherein m=0 (or n=0), i.e. a cyclopentadienyl group (having no substituent other than the crosslinking group Q). In the case of the conjugated five-membered ring groups having a substituent wherein m≠0 (or n≠0), a specific example of $R^1$ (or $R^2$) is a hydrocarbyl group having 1 to 20 carbon atoms, preferably 1 to 12 carbon atoms. The hydrocarbyl group may be bonded as a monovalent group to a cyclopentadienyl group or two of the hydrocarbyl groups may be bonded with each other to form a ring together with portion of the cyclopentadienyl group to which they are attached. Typical example of the latter is the one in which two of $R^1$ (or $R^2$) form a fused six-membered ring with a double bond of the cyclopentadienyl group in common, i.e. the one in which the conjugated five-membered ring groups is an indenyl group or a fluorenyl group. The typical examples of the conjugated five-membered ring groups are thus cyclopentadienyl group, an indenyl group and a fluorenyl group.

$R^1$ and $R^2$, respectively, include, in addition to the above-described hydrocarbyl group having 1 to 20 carbon atoms, preferably 1 to 12 carbon atoms, a halogen atom such as chlorine, fluorine, bromine, an alkoxy group such as the one having 1 to 12 carbon atoms, a silicon-containing hydrocarbyl group such as the one which contains silicon atom in the form of $-Si(R^a)(R^b)(R^c)$ wherein $R^a$, $R^b$ and $R^c$ each have 1 to 24 carbon atoms, a phosphorus-containing hydrocarbyl group such as the one which contains phosphorus atom in the form of $-P(R^a)(R^b)$ wherein $R^a$ and $R^b$ each have 1 to about 18 carbon atoms, a nitrogen-containing hydrocarbyl group such as the one which contains nitrogen atom in the form of $-N(R^a)(R^b)$ wherein $R^a$ and $R^b$ each have 1 to about 18 carbon atoms, and a boron-containing hydrocarbyl group such as the one which contains boron atom in the form of $-B(R^a)(R^b)$ wherein $R^a$ and $R^b$ each have 1 to about 18 carbon atoms. When m (or n) is at least 2 and at least two $R^1$s (or $R^2$s) are present, these groups may be the same or different.

Q is a bonding group which crosslinks the two conjugated five-membered ring groups. Particularly, it is (a) a lower alkylene group or a cycloalkylene group which may or may not be substituted by an alkyl, alicyclic and/or aromatic group having 1 to 15 carbon atoms, such as a methylene group, an ethylene group, an isopropylene group, a phenylmethylmethylene group, a diphenylmethylene group, a cyclohexylene group and the like, (b) a substituted or non-substituted silylene or oligosilylene group which may or may not be substituted by an alkyl, alicyclic and/or aromatic group having 1 to 12 carbon atoms such as a silylene group, a dimethylsilylene group, a phenylmethylsilylene group, a diphenylsilylene group, disilylene group, a tetramethyldisilylene group and the like, and (c) a hydrocarbyl group containing germanium, phosphorus, nitrogen or aluminum such as $(CH_3)_2Ge=$, $(C_6H_5)_2Ge=$, $(CH_3-)-P=$, $(C_6H_5-)-P=$, $(C_4H_9-)-N=$, $(C_6H_5-)-N=$, $(CH_3-)-B=$, $(C_4H_9-)-B=$, $(C_6H_5-)-B=$, $(C_6H_5-)-Al=$, $(CH_3-)-Al=$ and the like. Q is preferably an alkylene group or a substituted silylene group.

Me is a transition metal of the IVB-VIB group in the Periodic Table, preferably titanium, zirconium or hafnium.

X and Y, respectively, include hydrogen atom, a halogen atom, a hydrocarbyl group having 1 to 20, preferably 1 to 12 carbon atoms, an alkoxy group having 1 to 20, preferably 1 to 10 carbon atoms, an amino group, a phosphorus-containing hydrocarbyl group having 1 to 20, preferably 1 to 12 carbon atoms such as diphenylphosphine group, and a silicon-containing hydrocarbyl group having 1 to 20, preferably 1 to 10 carbon atoms such as trimethylsilyl. X and Y may be the same or different. m and n denote an integer of $0 \leq m \leq 4$ and $0 \leq n \leq 4$, respectively.

Specific examples of the transition metal compound in which Me is zirconium are specified in the following.

(a) Transition metal compounds containing a five-membered ring ligand crosslinked with an alkylene group:

Methylenebis(indenyl)zirconium chloride,
Ethylenebis(indenyl)zirconium chloride,
Ethylenebis(indenyl)zirconium monohydride monochloride
Ethylenebis(indenyl)methylzirconium monochloride, Ethylenebis(indenyl)zirconium monomethoxy monochloride
Ethylenebis(indenyl)zirconium diethoxide,
Ethylenebis(indenyl)zirconium dimethyl,
Ethylenebis(4,5,6,7-tetrahydroindenyl)zirconium dichloride,
Ethylenebis(2-methylindenyl)zirconium dichloride,
Ethylenebis(2,4-dimethylindenyl)zirconium dichloride,
Ethylenebis(2,4,7-trimethylindenyl)zirconium dichloride,
Ethylene(2,4-dimethylcyclopentadienyl)(3',5'-dimethylcyclopentadienyl)zirconium dichloride,
Ethylene(2-methyl-4-tert-butylcyclopentadienyl)(3'-tert-butyl-5'-methylcyclopentadienyl)zirconium dichloride,
Ethylene(2,3,5-trimethylcyclopentadienyl)(2',4',5'-trimethylcyclopentadienyl)zirconium dichloride,
Isopropylidenebis(indenyl)zirconium dichloride,
Isopropylidenebis(2,4-dimethylcyclopentadienyl)(3',5'-dimethylcyclopentadienyl)zirconium dichloride,
Isopropylidenebis(2-methyl-4-tert-butylcyclopentadienyl)(3'-tert-butyl-5'-methylcyclopentadienyl)zirconium dichloride,
Methylene(cyclopentadienyl)(3,4-dimethylcyclopentadienyl)zirconium dichloride,
Methylene(cyclopentadienyl)(3,4-dimethylcyclopentadienyl)zirconium chloride hydride,
Methylene(cyclopentadienyl)(3,4-dimethylcyclopentadienyl)zirconium dimethyl,
Methylene(cyclopentadienyl)(3,4-dimethylcyclopentadienyl)zirconium diphenyl,
Methylene(cyclopentadienyl)(trimethylcyclopentadienyl)zirconium dichloride,
Methylene(cyclopentadienyl)(tetramethylcyclopentadienyl)zirconium dichloride,
Isopropylidene(cyclopentadienyl)(3,4-dimethylcyclopentadienyl)zirconium dichloride,
Isopropylidene(cyclopentadienyl)(2,3,4,5-tetramethylcyclopentadienyl)zirconium dichloride,
Isopropylidene(cyclopentadienyl)(3-methylindenyl)zirconium dichloride,
Isopropylidene(cyclopentadienyl)(fluorenyl)zirconium dichloride,
Isopropylidene(2-methylcyclopentadienyl)(fluorenyl)zirconium dichloride,
Isopropylidene(2,5-dimethylcyclopentadienyl)(3,4-dimethylcyclopentadienyl)zirconium dichloride,
Isopropylidene(2,5-dimethylcyclopentadienyl)(fluorenyl)zirconium dichloride,
Ethylene(cyclopentadienyl)(3,5-dimethylcyclopentadienyl)zirconium dichloride,
Ethylene(cyclopentadienyl)(fluorenyl)zirconium dichloride,
Ethylene(2,5-dimethylcyclopentadienyl)(fluorenyl)zirconium dichloride,
Ethylene(2,5-diethylcyclopentadienyl)(fluorenyl)zirconium dichloride,
Diphenylmethylene(cyclopentadienyl)(3,4-dimethylcyclopentadienyl)zirconium dichloride,
Diphenylmethylene(cyclopentadienyl)(3,4-diethylcyclopentadienyl)zirconium dichloride,
Cyclohexylidene(cyclopentadienyl)(fluorenyl)zirconium dichloride, and
Cyclohexylidene(2,5-dimethylcyclopentadienyl)(3',4'-dimethylcyclopentadienyl)zirconium dichloride.

(b) Transition metal compounds containing a five-membered ring ligand crosslinked with a silylene group:
Dimethylsilylenebis(indenyl)zirconium dichloride,
Dimethylsilylene(4,5,6,7-tetrahydroindenyl)zirconium dichloride,
Dimethylsilylenebis(2-methylindenyl)zirconium dichloride,
Dimethylsilylenebis(2,4-dimethylindenyl)zirconium dichloride,
Dimethylsilylenebis(2,4,7-trimethylindenyl)zirconium dichloride,
Dimethylsilylene(2,4-dimethylcyclopentadienyl)(3',5'-dimethylcyclopentadienyl)zirconium dichloride,
Phenylmethylsilylenebis(indenyl)zirconium dichloride,
Phenylmethylsilylenebis(4,5,6,7-tetrahydroindenyl)zirconium dichloride,
Phenylmethylsilylene(2,4-dimethylcyclopentadienyl)(3',5'-dimethylcyclopentadienyl)zirconium dichloride,
Phenylmethylsilylene(2,3,5-trimethylcyclopentadienyl)(2,4,5-trimethylcyclopentadienyl)zirconium dichloride, Phenylmethylsilylenebis(tetramethylcyclopentadienyl)zirconium dichloride,
Diphenylsilylenebis(indenyl)zirconium dichloride,
Tetramethyldisilylenebis(indenyl)zirconium dichloride,
Tetramethyldisilylenebis(cyclopentadienyl)zirconium dichloride,
Tetramethyldisilylene(3-methylcyclopentadienyl)(indenyl)zirconium dichloride,
Dimethylsilylene(cyclopentadienyl)(3,4-dimethylcyclopentadienyl)zirconium dichloride,
Dimethylsilylene(cyclopentadienyl)(trimethylcyclopentadienyl)zirconium dichloride,
Dimethylsilylene(cyclopentadienyl)(tetramethylcyclopentadienyl)zirconium dichloride,
Dimethylsilylene(cyclopentadienyl(3,4-diethylcyclopentadienyl)zirconium dichloride,
Dimethylsilylene(cyclopentadienyl)(triethylcyclopentadienyl)zirconium dichloride,
Dimethylsilylene(cyclopentadienyl)(tetraethylcyclopentadienyl)zirconium dichloride,
Dimethylsilylene(cyclopentadienyl)(fluorenyl)zirconium dichloride,
Dimethylsilylene(cyclopentadienyl)(2,7-di-tert-butylfluorenyl)zirconium dichloride,
Dimethylsilylene(cyclopentadienyl)(octahydrofluorenyl)zirconium dichloride,
Dimethylsilylene(2-methylcyclopentadienyl)(fluorenyl)zirconium dichloride,
Dimethylsilylene(2,5-dimethylcyclopentadienyl)(fluorenyl)zirconium dichloride,
Dimethylsilylene(2-ethylcyclopentadienyl)(fluorenyl)zirconium dichloride,
Dimethylsilylene(2,5-diethylcyclopentadienyl)(fluorenyl)zirconium dichloride,
Dimethylsilylene(2-methylcyclopentadienyl)(2,7-di-tert-butylfluorenyl)zirconium dichloride,
Dimethylsilylene(2,5-dimethylcyclopentadienyl)(2,7-di-tert-butylfluorenyl)zirconium dichloride,
Dimethylsilylene(2-ethylcyclopentadienyl)(2,7-di-tert-butylfluorenyl)zirconium dichloride,
Dimethylsilylene(diethylcyclopentadienyl(2,7-di-tert-butylfluorenyl)zirconium dichloride,
Dimethylsilylene(methylcyclopentadienyl)(octahydrofluorenyl)zirconium dichloride,
Dimethylsilylene(dimethylcyclopentadienyl)(octahydrofluorenyl)zirconium dichloride,
Dimethylsilylene(ethylcyclopentadienyl)(octahydrofluorenyl)zirconium dichloride, and
Dimethylsilylene(diethylcyclopentadienyl)(octahydrofluorenyl)zirconium dichloride.

(c) Transition metal compounds containing a five-membered ligand crosslinked with a hydrocarbylated germanium, aluminum, boron, phosphorus or nitrogen:
Dimethylgermaniumbis(indenyl)zirconium dichloride,
Dimethylgermanium(cyclopentadienyl)(fluorenyl)zirconium dichloride,
Methylaluminumbis(indenyl)zirconium dichloride,
Phenylaluminumbis(indenyl)zirconium dichloride,
Phenylphosphinobis(indenyl)zirconium dichloride,
Ethylboranobis(indenyl)zirconium dichloride,
Phenylaminobis(indenyl)zirconium dichloride, and
Phenylamino(cyclopentadienyl)(fluorenyl)-zirconium dichloride.

(d) The aforementioned compounds (a) to (c) of which chlorine has been substituted by the other substituents such as bromine, iodine, hydride, methyl, phenyl, butoxy, phenoxy, trimethylsilyl or trimethylsilylmethyl can also be used.

In the present invention, the aforementioned compounds (a) to (d) of which the central metal, zirconium, has been substituted by the other metal such as titanium, hafnium, niobium, molybdenum or wolfram can also be used. Among these compounds, the zirconium compounds, the hafnium compounds and the titanium compounds are preferred. The zirconium compounds and hafnium compounds crosslinked with an alkylene group or a silylene group are more preferred.

Component (B)

The component (B) used in the present invention is a novel methylisobutylalumoxane represented by the formula

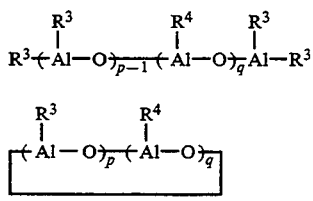

wherein $R^3$ and $R^4$ represent a methyl group or an isobutyl group, respectively. The methyl group and the isobutyl group are arranged in block or at random in the molecule, the latter being preferable. p and q denote an integer of at least 1, respectively, and the sum of $p+q$ is generally in the range of 2 to 100, preferably 4 to 50, more preferably 8 to 20. The ratio of p to q is in the range of 4:1 to 1:4, preferably 2:1 to 1:2. If the ratio is not within the range, the property of the component (B) approaches the one of methylalumoxane or isobutylalumoxane, and the specific advantages inherent in the present invention will not be attainable.

It is to be understood that the suffix "p" in the formulae (I) and (II) indicates the amount in the molecule of the unit

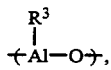

but does not indicate, when it is 2 or more, that units are in block connected in succession. The unit can thus be comprised in the molecule in block or at random. The same applies to the suffix "q".

A methyl group and an isobutyl group can be determined quantitatively by the $^{13}$C-NMR or $^1$H-NMR measurements of these groups or by the gas chromatographical analysis of hydrolysates generated by the reaction with water.

The polymerization degree or the molecular weight of the alumoxane compound can be determined, for example, by the cryoscopic method of benzene.

The alumoxane of the present invention gives a characteristic spectrum in the $^{27}$Al-NMR measurement. In other words, while an ordinary alkylaluminum shows a peak at a chemical shift in the range of 150 to 155 ppm which is characteristic to the coordination number of 4 and having a half-width of 2,000 Hz or less, the alumoxane of the present invention distinctively shows a peak at a chemical shift in the range of 160 ppm to 250 ppm and having a half-width of no smaller than 3,000 Hz. According to the present invention, the alumoxane shows preferably a peak at a chemical shift in the range of 160 ppm to 200 ppm, more preferably in the range of 165 ppm to 190 ppm, most preferably in the range of 165 ppm to 180 ppm and having a half-width of 3,000 Hz or more, more preferably 3,500 Hz or more, most preferably in the range of 4,000 Hz to 10,000 Hz.

In this connection, the NMR spectra ($^{13}$C: 67.9 MHz; $^{27}$Al: 70.4 MHz) of the alumoxane compound are those obtained when 2.5 ml of a solution in toluene of the alumoxane compound in a concentration of 6 to 7% by weight based on aluminum atom and 0.5 ml of deuterobenzene and admixed and by the measurement is performed with an NMR spectrograph GSX-270 model manufactured by Japan Electron Optics Laboratory Co., Ltd. at 27° C. $^{27}$Al-NMR spectra are those measured under the conditions of a pulse width of 90°, a pulse interval of 0.06 second and a scanning number of 10,000 at the non-decoupling mode. The chemical shift of $^{27}$Al is measured in relation to the $[Al(H_2O)_6]^{3+}$ ions in an aqueous aluminum sulfate solution as the external standard (0 ppm). The half-widths of spectra are calculated from the peak width at the half height and represented by Hz. $^{13}$C-NMR spectra are measured under the conditions of a pulse width of 45°, a pulse interval of 5 seconds and a scanning number of 1,000 at the proton-decoupling mode with a tetramethylsilane as the external standard (0 ppm).

Any methods for preparing the methylisobutylalumoxane compound which satisfies the conditions that the molar ratio of the methyl group to the isobutyl group is in the range of 4:1 to 1:4 and the $^{27}$Al-NMR spectrum has a chemical shift in the range of 160 to 250 ppm and a half-width in the range of no smaller than 3,000 Hz can be used as far as the alumoxane having such features can be obtained, but specific examples of the methods include:

(i) a method where trimethylaluminum and triisobutylaluminum are admixed in a mole ratio of 4:1 to 1:4 and the admixture is reacted under heating with a controlled amount of water or an inert organic solvent such as toluene, benzene or ether to which water has been saturated, (ii) a method where trimethylaluminum and triisobutylaluminum are admixed in a mole ratio of 4:1 to 1:4 and the admixture is reacted under heating at a temperature no lower than 50° C. with a salt hydrate having water of crystallization such as a hydrate of copper sulfate or aluminum sulfate, (iii) a method where silica gel is impregnated with water, which is treated with triisobutylaluminum and then with trimethylaluminum under heating, (iv) a method where methylalumoxane and isobutylalumoxane are synthesized respectively according to the well-known methods, the predetermined amounts of these two products are admixed, followed by heating to conduct the reaction and (v) a method where dimethylaluminum chloride are reacted with water and then, under heating, with isobutylmagnesium chloride.

It is preferable that the reactions in the methods (i) to (v) given above be conducted, or comprise a step conducted, at a temperature no lower than 50° C. The reaction or step at such a high temperature may produce the change in the spectrum of $^{27}$Al-NMR required in the present invention.

Formation of Catalyst

The catalyst of the present invention can be obtained by contacting the aforementioned components (A) and (B) within or outside a polymerization vessel in the presence or absence of a monomer to be polymerized.

Although the components (A) and (B) used in the present invention may be used in any amounts, they are generally used in such amounts that the atomic ratio of the aluminum atom in the component (B) to the transition metal in the component (A) (Al/Me) are in the range of 0.01 to 100,000, preferably 0.1 to 30,000. The contact methods of these components being not critical, the components may be introduced separately and contacted with each other, or the components which have been preliminarily contacted may also be used.

The catalyst according to the present invention, as described above, can comprise other components in addition to the components (A) and (B). A third or optional component which can be added to the components (A) and (B) include, for example, an active hydrogen containing compound such as $H_2O$, methanol, ethanol and butanol, an electron donating compound such as an ether, an ester and an amine, a hydrocarbyloxy-containing compound such as phenyl borate, dimethylmethoxyaluminum, phenyl phosphite, tetraethoxysilane and diphenyldimethoxysilane, and a Lewis acid such as triphenylborane, tris(pentafluorophenyl)-borane and triphenylphosphine.

<Polymerization of Olefins>

The catalyst for olefin polymerization according to the present invention is applied not only to the ordinary slurry polymerization but also to the liquid phase solvent-free polymerization in which substantially no solvent is used, the solution polymerization or the vapor phase polymerization methods. It is also applied to the fashions or modes of continuous polymerization, batchwise polymerization or preliminary polymerization. Therefore, the process for producing olefin polymers according to the present invention comprises contacting an olefin with the catalyst in the aforementioned polymerization methods or the polymerization fashions.

As the polymerization solvent in the case of slurry polymerization, saturated aliphatic or aromatic hydrocarbons such as hexane, heptane, pentane, cyclohexane, benzene or toluene are used alone or in combination. Polymerization is carried out at a temperature of −78° C. to about 200° C., preferably 0° C. to 150° C., and hydrogen can be used subsidiarily as a molecular weight modifier. In the case of slurry polymerization, the component (A) is used preferably in an amount of 0.0001 to 1.0 g per liter of the solvent.

The olefins polymerized in the presence of the catalyst system according to the present invention, or in other words, the olefins to be contacted with the catalyst according to the present invention for polymerization, are represented by the formula $R-CH=CH_2$, wherein R is a hydrogen atom or a hydrocarbyl group having 1 to 10 carbon atoms, which may or may not be branched. Specific examples of the olefins include ethylene, propylene, butene-1, pentene-1, hexene-1, 4-methylpentene-1 and the like, preferably ethylene and propylene. In the case of the polymerization of these olefins, copolymerization of ethylene with the aforementioned olefin in an amount of up to 50% by weight, preferably up to 20% by weight of ethylene can be carried out, and copolymerization of propylene with the aforementioned olefin, particularly ethylene, in an amount of up to 30% by weight of propylene can be carried out. Copolymerization of the olefin and the other copolymerizable monomers such as vinyl acetate, cyclic olefins or diolefins can also be carried out.

EXAMPLE

Example 1

Preparation of the component (A)

Ethylenebis(indenyl)zirconium dichloride was synthesized in accordance with the method described in J. Orgmet. Chem., (288) 63–67, 1985.

Preparation of the component (B)

In a 500 ml flask equipped with a stirrer and a reflux condenser which had been thoroughly purged with nitrogen, 200 ml of a dilute solution in hexane of isobutylalumoxane (manufactured by TOSO-AKZO; molecular weight: 1,525) (0.06M based on an aluminum atom) and 50 ml of a dilute solution in toluene of methylalumoxane (manufactured by TOSO-AKZO; molecular weight: 1,232) (0.06M based on an aluminum atom) were admixed. The admixture was heated to a temperature of 70° C. and reacted for 4 hours. After the reaction was completed, the solvent was removed by distillation under reduced pressure to give 18.1 g of a white solid which was methylisobutylalumoxane. The white solid was dissolved in toluene and the $^{13}$C-NMR measurement was conducted to give a spectrum illustrated in FIG. 1, in which the ratio of the methyl group to the isobutyl group was 1.16:1. The polymerization degree or the number of repeating of Al—O was 20 determined by the cryoscopic method of benzene. The $^{27}$Al-NMR measurement was conducted to give a spectrum as illustrated in FIG. 2, which had a peak at a chemical shift of 179 ppm with a half-width of 6196 Hz.

Polymerization of propylene

Into a stainless steel autoclave having an internal volume of 1.0 liter and equipped with a stirrer and a temperature regulator, 400 ml of thoroughly dehydrated and deoxygenated toluene, the catalyst component (B) of the present invention in an amount of 4 mmole based on an aluminum atom and ethylenebis(indenyl)zirconium dichloride in an amount of 0.418 mg (0.001 mmole) were introduced and propylene was polymerized at a propylene pressure of 7 kg/cm$^2$G and a polymerization temperature of 30° C. for 4 hours. After the polymerization was completed, the process product was taken into 3 liters of methanol, and the polymer was filtrated and dried to give 155 g of a product. The gel permeation chromatography of the polymer gave a number average molecular weight (Mn) of 25.1×10$^3$ and a molecular weight distribution as a ratio of weight average molecular weight to number average molecular weight of 1.92. As the $^{13}$C-NMR measurement with JEOL FX-200, the [mm] fraction of triad was 0.925.

Example 2

Preparation of the component (B)

Into a 1000 ml flask equipped with a stirrer and a reflux condenser which had been thoroughly purged with nitrogen was introduced 100 ml of dehydrated and deoxygenated toluene. Then, 0.72 g (10 mmole) of trimethylaluminum and 1.96 g (10 mmole) of triisobutylaluminum were dissolved in 50 ml of toluene in one of two dropping funnels and toluene saturated with water was introduced into another dropping funnel. The mixed aluminum solution and the saturated water containing toluene were fed at an equimolar rate of Al and H$_2$O over a period of 3 hours. After the feeding was completed, the mixture was heated up to a temperature of 50° C. and reacted for 2 hours. After the reaction was completed, the solvent was removed by distillation under reduced pressure to give 1.9 g of a white solid. The white solid was dissolved in toluene and the $^{13}$C-NMR measurement was conducted to give a spectrum, in which the ratio of the methyl group to the isobutyl group was 1:1.35. The polymerization degree was 17. The $^{27}$Al-NMR measurement was conducted to give a spectrum as illustrated in FIG. 3, which had a peak at a chemical shift of 174 ppm with a half-width of 5844 Hz.

Polymerization of propylene

Polymerization was carried out under the same condition as in Example 1 except that the catalyst component prepared above was used. There was recovered 148 g of a polymer, which had a number average molecular weight (Mn) of $23.7 \times 10^3$ and a molecular weight distribution of 1.95. The stereoregularity was 0.930 by the [mm] fraction of triad.

Comparative Examples 1, 2

The component (B) in Example 1 was replaced by a polymethylalumoxane (manufactured by TOSO-AKZO; molecular weight: 1,232) or a polymethylalumoxane (manufactured by SCHERING; molecular weight, not specified). The $^{27}$Al-NMR measurement gave spectra illustrated in FIGS. 4 and 5, which had a peak at a chemical shift of 152 ppm with a half-width of 1690 Hz and a peak at a chemical shift of 154 ppm with a half-width of 1549 Hz. An α-olefin was polymerized in the same manner as in Example 1. The results are shown in Table 1.

Comparative Example 3

The component (B) in Example 1 was replaced by a polyisobutylalumoxane (manufactured by TOSO-AKZO; molecular weight: 1,525) which gave the $^{27}$Al-NMR spectrum in FIG. 6. An α-olefin was polymerized in the same manner as in Example 1. The results are shown in Table 1.

Comparative Example 4

An olefin polymer was prepared in the same method as in Preparation Example 1 in Japanese Pat. Laid-Open Publication No. 247201/1990. That is, in a 500 ml flask thoroughly purged with nitrogen were placed 18.0 g of an isobutylalumoxane (manufactured by TOSO-AKZO; molecular weight: 1,525), 3.3 g of trimethylaluminum and 150 ml of toluene, and after it had been cooled to $-10°$ C., 0.83 g of deaerated water was dropped in the mixture over a period of 90 minutes. After the mixture was reacted at $-10°$ C. for 30 minutes, the temperature of it was raised up to room temperature over a period of 2 hours. The solvent of the reaction liquid thus obtained was removed by distillation under reduced pressure to give 19.1 g of white solid as a product. The $^{27}$Al-NMR spectrum of the alumoxane is illustrated in FIG. 7, and the results of the evaluation of the polymerization are shown in Table 1.

Comparative Example 5

An olefin polymer was prepared in the same method as in Preparation Example 2 in Japanese Pat. Laid-Open Publication No. 247201/1990. That is, in a 500 ml flask equipped with a stirrer and thoroughly purged with nitrogen were placed 26.0 g of an isobutylalumoxane (manufactured by TOSO-AKZO; molecular weight: 1,525), 11.4 g of methylalumoxane and 350 ml of toluene, and after it had been cooled to $-10°$ C., 0.53 g of deaerated water was dropped in the mixture over a period of 1 hour. After the mixture was reacted at $-10°$ C. for 30 minutes, the temperature of it was raised up to room temperature over a period of 2 hours. The solvent of the reaction solution thus obtained was removed by distillation under reduced pressure to give 30.6 g of an alumoxane as a product. The $^{27}$Al-NMR spectrum of the alumoxane is illustrated in FIG. 8, and the results of the evaluation of the polymerization are shown in Table 1.

TABLE 1

| | Remarks | i-Bu/Me (molar ratio) | $^{27}$Al-NMR Chemical shift (ppm) | Half-width (Hz) | Polymerization activity (g-polymer/-g-catalyst) | Number average molecular weight (Mn) | Molecular weight distribution (Mw/Mn) | Stereo regularity [mm] |
|---|---|---|---|---|---|---|---|---|
| Example 1 | | 0.86 | 179 | 6196 | $37.1 \times 10^4$ | $25.1 \times 10^3$ | 1.92 | 0.925 |
| Example 2 | | 1.35 | 174 | 5844 | $35.4 \times 10^4$ | $23.7 \times 10^3$ | 1.95 | 0.930 |
| Comparative Example 1 | Methylalumoxane (TOSO-AKZO) | — | 152 | 1690 | $19.5 \times 10^4$ | $20.3 \times 10^3$ | 1.98 | 0.914 |
| Comparative Example 2 | Methylalumaxane (SCHERING) | — | 154 | 1549 | $17.3 \times 10^4$ | $20.1 \times 10^3$ | 1.99 | 0.925 |
| Comparative Example 3 | Isobutylalumoxane (TOSO-AKZO) | — | 67 | 7504 | No activity | | | |
| Comparative Example 4 | Trace run of Example 1, Japanese Patent Laid-open Publication No. 247201/1990 | 1.05 | 156 | 2240 | $8.1 \times 10^4$ | $18.4 \times 10^3$ | 1.98 | 0.915 |
| Comparative Example 5 | Trace run of Example 2, Japanese Patent Laid-Open Publication | 1.30 | 155 or 66 | — | $11.6 \times 10^4$ | $19.7 \times 10^3$ | 1.96 | 0.922 |

| Remarks | i-Bu/Me (molar ratio) | $^{27}$Al-NMR Chemical shift (ppm) | Half-width (Hz) | Polymerization activity (g-polymer/-g-catalyst) | Number average molecular weight (Mn) | Molecular weight distribution (Mw/Mn) | Stereo regularity [mm] |
|---|---|---|---|---|---|---|---|
| No. 247201/1990 | | | | | | | |

Example 3

Preparation of the catalyst component (A)

Dimethylsilylenebis(tetrahydroindenyl)zirconium dichloride was synthesized by the method described in J. Orgmet. Chem., (342) 21–29, 1988 and J. Orgmet. Chem., (369) 359–370, 1989.

Specifically, in a 300 ml flask which had been thoroughly purged with nitrogen, 5.4 g of bis(indenyl)dimethylsilane was diluted in 150 ml of tetrahydrofuran and cooled to a temperature of no higher than −50° C., and the 23.6 ml of n-butyllithium (1.6M/liter) was added dropwise to the solution over a period of 30 minutes. After the addition was completed, the mixture was raised to room temperature over a period of 1 hour and reacted at room temperature for four hours to give the reaction liquid A.

Into a 500 ml flask purged with nitrogen, 200 ml of tetrahydrofuran was introduced and cooled to a temperature of no higher than −50° C., and 4.38 g of zirconium tetrachloride was slowly introduced. After the total amount of the reaction liquid A was then introduced into the flask, the mixture was slowly warmed to room temperature over a period of 3 hours. After the mixture was reacted at room temperature for 2 hours, it was warmed to a temperature of 60° C. and further reacted for 2 hours. After the reaction was completed, the solvent was removed by distillation under reduced pressure, and the residue was dissolved in 100 ml of toluene. The solvent was removed again by distillation under reduced pressure to give 3.86 g of crude crystals of dimethylsilylenebis(indenyl)zirconium dichloride.

The crude crystals were then dissolved in 150 ml of dichloromethane and introduced into a 500 ml autoclave. After a platinum-on-carbon catalyst (0.5% by weight of platinum supported on carbon) was introduced into the autoclave, hydrogenation was conducted under a hydrogen pressure of 50 kg/cm$^2$G at 50° C. for 5 hours. After the hydrogenation was completed, the catalyst was removed by filtration and the solvent was removed by distillation under reduced pressure. The residue was subjected to extraction with toluene and recrystallized from a solvent to give 1.26 g of the dimethylsilylenebis(tetrahydroindenyl)zirconium dichloride desired.

Polymerization of propylene

Propylene was polymerized in the same manner as in Example 1 except that 0.456 mg (0.001 mmole) of dimethylsilylenebis(tetrahydroindenyl)zirconium dichloride obtained above was introduced. The results are shown in Table 2.

Comparative Example 6

Propylene was polymerized under the same conditions as in Example 3 except that 0.001 g of the component (A) in Example 3 and 4 mmole of methylalumoxane (manufactured by TOSO-AKZO) were used. The results are shown in Table 2.

Example 4, Comparative Example 7

Preparation of the component (A)

Preparation of isopropylidene(cyclopentadienyl)(fluorenyl)zirconium dichloride

After 200 ml of THF and 16.5 g of fluorene were introduced into a 500 ml flask purged with nitrogen and cooled to a temperature of no higher than −50° C., 67 ml of a dilute solution in diethyl ether of methyllithium (1.4 mole) was added dropwise over a period of 30 minutes and the mixture was slowly warmed to room temperature and reacted for 3 hours. After the mixture was cooled again to a temperature of at least −50° C., 10 g of 6,6-dimethylfulvene was added dropwise to the mixture over a period of 30 minutes. After the addition was completed, the mixture was warmed to room temperature and reacted for two days. After the reaction was completed, 60 ml of H$_{20}$ was added to stop the reaction, and the ether layer was separated and dried over anhydrous MgSO$_4$. The solvent was evaporated to dryness to give 17.6 g of crude crystals of 2-cyclopentadienyl-2-fluorenylpropane.

Next, 10 g of the aforementioned crude crystals were dissolved in 100 ml of THF and cooled to a temperature of no higher than −50° C., and 46.0 ml (0.0736 mole) of n-butyllithium was added dropwise over a period of 10 minutes. The mixture was warmed to room temperature over 1 hour and reacted at the temperature for 2 hours. After the solvent was evaporated to dryness under nitrogen stream, 100 ml of dichloromethane was added and the mixture was cooled to a temperature of no higher than −50° C. A solution of 8.16 g of zirconium tetrachloride in 50 ml of dichloromethane prepared at a lower temperature was then poured in lump into the mixture. After mixing, the resulting mixture was slowly warmed to room temperature over a period of 3 hours and reacted at room temperature for one day. After the reaction was completed, solids were removed by filtration and the filtrate was concentrated and recrystallized from a solvent to give 4.68 g of isopropylidene(cyclopentadienyl)(fluorenyl)zirconium dichloride as a red product.

Polymerization of propylene

Polymerization was conducted in the same manner as in Example 3 and Comparative Example 6 except that the aforementioned component (A) was used. The results are shown in Table 2.

Example 5

Polymerization of ethylene

After a stainless steel autoclave having an internal volume of 1.5 liters and equipped with a stirrer and a temperature regulator was thoroughly purged with ethylene, 500 ml of thoroughly dehydrated and deoxygenated n-heptane was introduced into the autoclave and 5 mmole of the component (B) obtained in Example 1, 0.46 mg (0.001 mmole) of the component (A) obtained in Example 3 and 300 cc of hydrogen were next introduced. Then, polymerization was conducted under an ethylene pressure of 7 kg/cm²G at 75° C. for 2 hours. The results are shown in Table 2.

Comparative Example 8

Polymerization was conducted under the same conditions as in Example 5 except that methylalumoxane of TOSO-AKZO was used in place of the component (B). The results are shown in Table 2.

Comparative Examples 9, 10

Polymerization was conducted under the same conditions as in Example 3 and Comparative Example 6 except that the component (A) used in these runs was replaced respectively by bis(cyclopentadienyl)zirconium dichloride. The results obtained are shown in Table 2.

drated and deoxygenated toluene, 10 ml of 1-hexene, 4 mmoles based on an aluminum atom of the component (B) obtained in Example 1 and 0.418 mg (0,001 mmole) of ethylenebis(indenyl)zirconium dichloride were introduced into the autoclave, and polymerization was conducted under an ethylene pressure of 5 kg/cm²G at a polymerization temperature of 50° C. for 2 hours. After the polymerization was completed, the process product was taken into methanol and the polymer was separated by filtration and dried. As a result, the polymer was recovered in an amount of 121.3 g. Gel permeation chromatography conducted on the polymer gave the number average molecular weight (Mn) of $18.7 \times 10^3$ and the molecular weight distribution as the ratio of weight average molecular weight/number average molecular weight of 1.78. The [mm] fraction of triad was 0.841 and the hexene content was 3.4% by mole.

TABLE 2

| | Components (A) | Components (B) | Monomer Polymerized | Polymerization activity g-polymer/-g-catalyst | Number average molecular weight (Mn) | Molecular weight distribution (Mw/Mn) | Stereo regularity [mm] or [rr] |
|---|---|---|---|---|---|---|---|
| Example 3 | Dimethylsilylenebis-(tetrahydroindenyl)-zirconium dichloride | Component (B) in Example 1 | Propylene | 238,000 | 215,000 | 1.98 | [mm] 0.921 |
| Comparative Example 6 | ibid. | Methylalumoxane (TOSO-AKZO) | ibid. | 166,000 | 13,300 | 2.38 | [mm] 0.910 |
| Example 4 | Isopropylidene-(cyclopentadienyl)-(fluorenyl)zirconium dichloride | Component (B) in Example 1 | ibid. | 203,000 | 35,700 | 2.29 | [rr] 0.855 |
| Comparative Example 7 | ibid. | Methylalumoxane (TOSO-AKZO) | ibid. | 149,900 | 28,600 | 2.12 | [mm] 0.847 |
| Example 5 | Dimethylsilylenebis-(tetrahydroindenyl)-zirconium dichloride | Component (B) in Example 1 | Ethylene | 108,000 | 13,400 | 3.27 | — |
| Comparative Example 8 | ibid. | Methylalumoxane (TOSO-AKZO) | ibid. | 70,600 | 12,300 | 2.79 | — |
| Comparative Example 9 | Bis(cyclopentadienyl)-zirconium dichloride | Component (B) in Example 1 | Propylene | 10,200 | 1,150 | 1.65 | [mm] 0.257 |
| Comparative Example 10 | ibid. | Methylalumoxane (TOSO-AKZO) | ibid. | 13,500 | 1,120 | 1.64 | 0.252 |

Example 6

Polymerization of ethylene/1-hexene

After a stainless steel autoclave having an internal volume of 1.5 liters and equipped with a stirrer and a temperature regulator was thoroughly purged with ethylene, 415 ml of thoroughly dehydrated and deoxygenated n-heptane and 85 ml of hexene were introduced into the autoclave. Then, 3 mmole of the component (B) obtained in Example 1 and 0.46 mg (0.001 mmole) of the component (A) obtained in Example 3 were introduced, and polymerization was conducted under an ethylene pressure of 7 kg/cm²G at 70° C. for 2 hours. After the polymerization was completed, 50 ml of ethanol and 500 ml of water were added to the slurry obtained, and the organic layer was dried by evaporation to give 52.6 g of a polymer. Therefore, the polymerization activity of the catalyst was 114,300 (g polymer/g catalyst), the number average molecular weight was 57,000, Mw/Mn=2.62, and melting point was 107.2° C.

Example 7

Polymerization of propylene/1-hexene

Into a stainless steel autoclave having an internal volume of 1.0 liter and equipped with a stirrer and a temperature regulator, 400 ml of thoroughly dehy- Example 8

In a 500 ml autoclave was introduced a solution in 150 ml of 2.0 g of ethylenebis(indenyl)zirconium dichloride obtained in Example 1. 5 g of a catalyst of platinum-on-carbon containing 0.5% by weight of platinum was introduced, and hydrogenation was conducted under a hydrogen gas pressure of 50 kg/cm²G at 50° C. for 5 hours. After the reaction, the catalyst was removed and the solvent was distilled off in vacuo, and the residue was subjected to extraction with toluene and then to recrystallization, whereby 1.7 g of ethylenebis(4,5,6,7-tetrahydroindenyl)zirconium dichloride was recovered.

1.5 g of the crystal thus recovered was dissolved in 200 ml of tetrahydrofuran and cooled to −50° C. 10 mmol of methyllithium diluted in diethylether was added thereto, followed by warming to room temperature over 1 hour and then by reaction at room temperature for 8 hours. After the reaction, the solvent was distilled off in vacuo, the residue was subjected to extraction with toluene, followed by re-crystallization, whereby 0.9 g of ethylenebis(4,5,6,7-tetrahydroindenyl)zirconium dimethyl was obtained.

Polymerization of propylene was conducted in the same manner as in Example 1 except that the component (A) thus obtained was used.

The result obtained was shown in Table 3.

Comparative Example 11

Polymerization of propylene was conducted in the same manner as in Comparative Example 1 except that the component (A) prepared in Example 8 was used. The result obtained is shown in Table 3.

TABLE 3

| | Components (A) | Components (B) | Monomer Polymerized | Polymerization activity g-polymer/-g-catalyst) | Number average molecular weight (Mn) | Molecular weight distribution (Mw/Mn) | Stereo regularity [mm] or [rr] |
|---|---|---|---|---|---|---|---|
| Example 8 | Ethylenebis(4,5,6,7-tetrahydroindenyl)-zirconium dimethyl | Component (B) in Example 1 | Propylene | 265,000 | 41,500 | 2.05 | 0.930 |
| Comparative Example 11 | ibid. | Methylalumoxane (TOSO-AKZO) | ibid. | 157,000 | 37,800 | 2.10 | 0.922 |

What is claimed is:

1. A catalyst for α-olefin polymerization which comprises the following components (A) and (B):

component (A), which is a transition metal compound represented by the formula $$Q(C_5H_{4-m}R^1_m)(C_5H_{4-n}R^2_n)MeXY$$

wherein $(C_5H_{4-m}R^1_m)$ and $(C_5H_{4-n}R^2_n)$ respectively represent a conjugated five-membered ring ligand coordinating to a metal Me; $R^1$ and $R^2$, which may be the same or different and a plurality of each of which can be bonded together, respectively represent a hydrocarbyl group having 1 to 20 carbon atoms, a halogen atom, an alkoxy group, a silicon-containing hydrocarbyl group, a phosphorus-containing hydrocarbyl group, a nitrogen-containing hydrocarbyl group or a boron-containing hydrocarbyl group; Q represents a bonding group which crosslinks the two conjugated five-membered ring ligands; Me represents a transition metal of the IVB-VIB group in the Periodic Table; X and Y, which may be the same or different, respectively represent hydrogen, a halogen atoms, a hydrocarbyl group, an alkoxy group, an amino group, a phosphorus-containing hydrocarbyl group or a silicon-containing hydrocarbyl group; m denotes an integer of $0 \leq m \leq 4$ and n denotes an integer of $0 \leq n \leq 4$;

component (B), which is a methylisobutylalumoxane which satisfies the following conditions (a), (b) and (c):

(a) the molar ratio of a methyl group to an isobutyl group is in the range of 4:1 to 1:4, (b) the chemical shift of $^{27}$Al-NMR is in the range of 160 ppm to 250 ppm and the peak has a half-height width of no smaller than 3000 Hz, and (c) it has a repeating unit of Al—O in an amount of 2 to 100.

2. The catalyst for α-olefin polymerization according to claim 1, wherein the groups $(C_5H_{4-m}R^1_m)$ and $(C_5H_{4-n}R^2_n)$ of said transition metal compound are the same.

3. The catalyst for α-olefin polymerization according to claim 1, wherein the groups $(C_5H_{4-m}R^1_m)$ and $(C_5H_{4-n}R^2_n)$ are selected from the group consisting of substituted or non-substituted cyclopentadienyl, indenyl and fluorenyl groups, respectively.

4. The catalyst for α-olefin polymerization according to claim 1, wherein Q is (a) a lower alkylene group or a cycloalkylene group which may or may not have a substituent that is an alkyl, alicyclic and/or aromatic group and has 1 to 15 carbon atoms, (b) a silylene or oligosilylene group which may or may not have a substituent that is an alkyl, alicyclic and/or aromatic group and has 1 to 12 carbon atoms, and (c) a hydrocarbyl group containing therein an element selected from the group consisting of germanium, phosphorus, nitrogen, boron and aluminum.

5. The catalyst for α-olefin polymerization according to claim 4, wherein Q is a lower alkylene group which may or may not have a substituent that is an alkyl, alicyclic and/or aromatic group and has 1 to 15 carbon atoms or a silylene or oligosilylene group which may or may not have a substituent that is an alkyl, alicyclic and/or aromatic group and has 1 to 12 carbon atoms.

6. The catalyst for α-olefin polymerization according to claim 1, wherein Me is titanium, zirconium or hafnium.

7. The catalyst for α-olefin polymerization according to claim 1, wherein X and Y contain 1 to 20 carbon atoms when they have a hydrocarbyl moiety, respectively.

8. The catalyst for α-olefin polymerization according to claim 1, wherein the methylisobutylalumoxane is represented by the following formula (I) or (II):

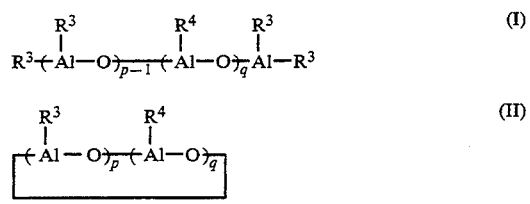

wherein $R^3$ and $R^4$ represent a methyl group or an isobutyl group, respectively, the methyl group and the isobutyl group being arranged in block or at random in the molecule; p and q denote an integer of at least 1, respectively, the sum of p+q being in the range of 2 to 100; and the ratio of p to q is in the range of 4:1 to 1:4.

9. The catalyst for α-olefin polymerization according to claim 8, wherein the sum of p+q is in the range of 4 to 50.

10. The catalyst for α-olefin polymerization according to claim 8, wherein the sum of p+q is in the range of 8 to 20.

11. The catalyst of claim 1, wherein said $^{27}$Al-NMR of said methylisobutylalumoxane is obtained when 2.5 mL of a toluene solution of said methylisobutylalumoxane compound, in a concentration of 6 to 7% by weight based on aluminum atoms, and 0.5 mL of deutero-benzene are admixed.

12. A methylisobutylalumoxane which satisfies the following conditions:

(a) the molar ratio of a methyl group to an isobutyl group is in the range of 4:1 to 1:4, (b) the chemical shift of $^{27}$AL-NMR is in the range of 160 ppm to 250 ppm and the peak has a half-height width of no smaller than 3000 Hz, and (c) it has a repeating unit of Al—O in an amount of 2 to 100 as combined with a compound of the group IVB to VIB of the Periodic Table having at least one π electron conjugated ligand to form a catalyst for polymerization of α-olefins.

* * * * *